US009889256B2

(12) United States Patent
Cabiri et al.

(10) Patent No.: US 9,889,256 B2
(45) Date of Patent: Feb. 13, 2018

(54) SENSING A STATUS OF AN INFUSER BASED ON SENSING MOTOR CONTROL AND POWER INPUT

(71) Applicant: MEDIMOP Medical Projects Ltd., Ra'anana (IL)

(72) Inventors: Oz Cabiri, Macabim-Reut (IL); Reuven Y. Filman, Netanya (IL)

(73) Assignee: MEDIMOP MEDICAL PROJECTS LTD., Ra'anana (IL)

( * ) Notice: Subject to any disclaimer, the term of this patent is extended or adjusted under 35 U.S.C. 154(b) by 1009 days.

(21) Appl. No.: 13/886,867

(22) Filed: May 3, 2013

(65) Prior Publication Data

US 2014/0330240 A1 Nov. 6, 2014

(51) Int. Cl.
*A61M 5/172* (2006.01)
*A61M 5/168* (2006.01)
*A61M 5/142* (2006.01)

(52) U.S. Cl.
CPC ........ *A61M 5/172* (2013.01); *A61M 5/14244* (2013.01); *A61M 5/16831* (2013.01); *A61M 2005/16863* (2013.01); *A61M 2205/70* (2013.01)

(58) Field of Classification Search
CPC .............. A61M 5/172; A61M 5/14244; A61M 5/16831; A61M 2005/16863; A61M 2205/70
USPC .......................................................... 73/168
See application file for complete search history.

(56) References Cited

U.S. PATENT DOCUMENTS

| | | | |
|---|---|---|---|
| 3,946,732 | A | 3/1976 | Hurscham |
| 3,994,295 | A | 11/1976 | Wulff |
| 4,167,663 | A | 9/1979 | Granzow, Jr. et al. |
| 4,273,122 | A | 6/1981 | Whitney et al. |
| 4,396,385 | A | 8/1983 | Kelly et al. |
| 4,601,702 | A | 7/1986 | Hudson |
| 4,634,426 | A | 1/1987 | Kamen |
| 4,886,499 | A | 12/1989 | Cirelli et al. |

(Continued)

FOREIGN PATENT DOCUMENTS

| | | |
|---|---|---|
| CN | 101868273 A | 10/2010 |
| EP | 0401179 A1 | 12/1990 |

(Continued)

OTHER PUBLICATIONS

Office Action dated Nov. 25, 2015 in U.S. Appl. No. 14/372,384 by Cabiri.

(Continued)

*Primary Examiner* — Lisa Caputo
*Assistant Examiner* — Nathaniel T Woodward
(74) *Attorney, Agent, or Firm* — Panitch Schwarze Belisario & Nadel LLP

(57) ABSTRACT

A status of a battery operated infuser may be detected by measuring a controlled input parameter. The measurement may be used to determine a magnitude of the input parameter and a parameter of the control. For example, control of power input to a motor may be by pulse density modulation. An integral of current over time may serve as a measure of current magnitude and pulse density. The result of the integral may be used to determine the status of the injector. The status may include normal functions for example start of pumping and/or malfunctions such as occlusion or drive disengagement.

13 Claims, 9 Drawing Sheets

(56) References Cited

U.S. PATENT DOCUMENTS

| | | | |
|---|---|---|---|
| 4,908,014 A | 3/1990 | Kroyer | |
| 4,919,596 A | 4/1990 | Slate et al. | |
| 4,950,235 A * | 8/1990 | Slate | A61M 5/16831 |
| | | | 128/DIG. 13 |
| 4,950,246 A | 8/1990 | Muller | |
| 5,109,850 A | 5/1992 | Blanco et al. | |
| 5,131,816 A | 7/1992 | Brown et al. | |
| 5,254,096 A | 10/1993 | Rondelet et al. | |
| 5,342,313 A | 8/1994 | Campbell et al. | |
| 5,354,287 A | 10/1994 | Wacks | |
| 5,383,865 A | 1/1995 | Michel | |
| 5,411,482 A | 5/1995 | Campbell | |
| 5,501,665 A | 3/1996 | Jhuboo et al. | |
| 5,558,639 A * | 9/1996 | Gangemi | A61M 5/142 |
| | | | 222/325 |
| 5,593,390 A | 1/1997 | Castellano et al. | |
| 5,616,132 A | 4/1997 | Newman | |
| 5,643,218 A | 7/1997 | Lynn et al. | |
| 5,647,853 A | 7/1997 | Feldmann et al. | |
| 5,658,133 A | 8/1997 | Anderson et al. | |
| 5,690,618 A | 11/1997 | Smith et al. | |
| D393,314 S | 4/1998 | Meisner et al. | |
| 5,800,420 A | 9/1998 | Gross et al. | |
| 5,807,375 A | 9/1998 | Gross et al. | |
| 5,814,020 A | 9/1998 | Gross | |
| 5,851,197 A | 12/1998 | Marano et al. | |
| 5,858,001 A | 1/1999 | Tsals et al. | |
| 5,858,008 A | 1/1999 | Capaccio | |
| 5,931,814 A | 8/1999 | Alex et al. | |
| 5,957,895 A | 9/1999 | Sage et al. | |
| 5,993,423 A | 11/1999 | Choi | |
| 5,997,501 A | 12/1999 | Gross et al. | |
| 6,004,297 A | 12/1999 | Steenfeldt-Jensen et al. | |
| 6,064,797 A | 5/2000 | Crittendon et al. | |
| 6,074,369 A | 6/2000 | Sage et al. | |
| 6,175,688 B1 | 1/2001 | Cassidy et al. | |
| 6,186,982 B1 | 2/2001 | Gross et al. | |
| 6,200,289 B1 | 3/2001 | Hochman et al. | |
| 6,248,093 B1 | 6/2001 | Moberg | |
| 6,277,095 B1 | 8/2001 | Kriesel et al. | |
| 6,277,098 B1 | 8/2001 | Klitmose et al. | |
| 6,277,099 B1 | 8/2001 | Strowe et al. | |
| 6,287,283 B1 | 9/2001 | Ljunggreen et al. | |
| 6,362,591 B1 | 3/2002 | Moberg | |
| 6,391,005 B1 | 5/2002 | Lum et al. | |
| 6,423,029 B1 | 7/2002 | Elsberry | |
| 6,423,035 B1 | 7/2002 | Das et al. | |
| D465,026 S | 10/2002 | May et al. | |
| 6,458,102 B1 | 10/2002 | Mann et al. | |
| 6,485,461 B1 | 11/2002 | Mason et al. | |
| 6,485,465 B2 | 11/2002 | Moberg et al. | |
| 6,500,150 B1 | 12/2002 | Gross et al. | |
| 6,517,517 B1 | 2/2003 | Farrugia et al. | |
| D471,274 S | 3/2003 | Diaz et al. | |
| D471,983 S | 3/2003 | Hippolyte et al. | |
| 6,530,901 B1 | 3/2003 | Tsukada et al. | |
| 6,555,986 B2 | 4/2003 | Moberg | |
| 6,558,351 B1 | 5/2003 | Steil et al. | |
| 6,589,229 B1 | 7/2003 | Connelly et al. | |
| 6,595,956 B1 | 7/2003 | Gross et al. | |
| 6,595,960 B2 | 7/2003 | West et al. | |
| 6,645,181 B1 | 11/2003 | Lavi et al. | |
| 6,652,482 B2 | 11/2003 | Hochman | |
| 6,656,158 B2 | 12/2003 | Mahoney et al. | |
| 6,656,159 B2 | 12/2003 | Flaherty | |
| 6,659,980 B2 | 12/2003 | Moberg et al. | |
| 6,673,033 B1 | 1/2004 | Sciulli et al. | |
| 6,679,862 B2 | 1/2004 | Diaz et al. | |
| 6,699,218 B2 | 3/2004 | Flaherty et al. | |
| 6,749,587 B2 | 6/2004 | Flaherty | |
| 6,768,425 B2 | 7/2004 | Flaherty et al. | |
| 6,786,890 B2 | 9/2004 | Preuthun et al. | |
| 6,800,071 B1 | 10/2004 | McConnell et al. | |
| 6,805,687 B2 | 10/2004 | Dextradeur et al. | |
| 6,824,529 B2 | 11/2004 | Gross et al. | |
| 6,843,782 B2 | 1/2005 | Gross et al. | |
| 6,854,620 B2 | 2/2005 | Ramey | |
| 6,905,298 B1 | 6/2005 | Haring | |
| 6,908,452 B2 | 6/2005 | Diaz et al. | |
| 6,933,693 B2 * | 8/2005 | Schuchmann | F04B 49/065 |
| | | | 318/432 |
| 6,950,028 B2 | 9/2005 | Zweig | |
| 6,960,192 B1 | 11/2005 | Flaherty et al. | |
| 7,001,360 B2 | 2/2006 | Veasey et al. | |
| 7,048,715 B2 | 5/2006 | Diaz et al. | |
| 7,060,059 B2 | 6/2006 | Keith et al. | |
| 7,128,727 B2 | 10/2006 | Flaherty et al. | |
| 7,144,384 B2 | 12/2006 | Gorman et al. | |
| 7,193,521 B2 | 3/2007 | Moberg et al. | |
| D544,092 S | 6/2007 | Lewis | |
| 7,247,149 B2 | 7/2007 | Beyerlein | |
| 7,250,037 B2 | 7/2007 | Shermer et al. | |
| 7,267,669 B2 | 9/2007 | Staunton et al. | |
| 7,303,549 B2 | 12/2007 | Flaherty et al. | |
| 7,390,314 B2 | 6/2008 | Stutz, Jr. et al. | |
| 7,407,493 B2 | 8/2008 | Cane' | |
| 7,455,663 B2 | 11/2008 | Bikovsky | |
| 7,459,571 B2 | 12/2008 | Schlitter et al. | |
| 7,465,290 B2 | 12/2008 | Reilly | |
| 7,497,842 B2 | 3/2009 | Diaz et al. | |
| 7,524,304 B2 | 4/2009 | Genosar | |
| 7,530,964 B2 | 5/2009 | Lavi et al. | |
| 7,547,281 B2 | 6/2009 | Hayes et al. | |
| 7,563,253 B2 | 7/2009 | Tanner et al. | |
| 7,565,208 B2 | 7/2009 | Harris et al. | |
| 7,569,050 B2 | 8/2009 | Moberg et al. | |
| D600,341 S | 9/2009 | Loerwald | |
| 7,585,287 B2 | 9/2009 | Bresina et al. | |
| 7,588,559 B2 | 9/2009 | Aravena et al. | |
| D602,155 S | 10/2009 | Foley et al. | |
| D602,586 S | 10/2009 | Foley et al. | |
| D604,835 S | 11/2009 | Conley | |
| 7,621,893 B2 | 11/2009 | Moberg et al. | |
| 7,628,770 B2 | 12/2009 | Ethelfeld | |
| 7,628,772 B2 | 12/2009 | McConnell et al. | |
| 7,628,782 B2 | 12/2009 | Adair et al. | |
| 7,637,891 B2 | 12/2009 | Wall | |
| 7,641,649 B2 | 1/2010 | Moberg et al. | |
| 7,660,627 B2 | 2/2010 | McNichols et al. | |
| 7,678,079 B2 | 3/2010 | Shermer et al. | |
| 7,682,338 B2 | 3/2010 | Griffin | |
| 7,686,787 B2 | 3/2010 | Moberg et al. | |
| 7,699,829 B2 | 4/2010 | Harris et al. | |
| 7,699,833 B2 | 4/2010 | Moberg et al. | |
| 7,704,227 B2 | 4/2010 | Moberg et al. | |
| 7,704,231 B2 | 4/2010 | Pongpairochana et al. | |
| 7,708,717 B2 | 5/2010 | Estes et al. | |
| 7,713,238 B2 | 5/2010 | Mernoe | |
| 7,713,240 B2 | 5/2010 | Istoc et al. | |
| 7,717,913 B2 | 5/2010 | Novak et al. | |
| 7,722,574 B2 | 5/2010 | Toman et al. | |
| 7,736,344 B2 | 6/2010 | Moberg et al. | |
| 7,744,589 B2 | 6/2010 | Mounce et al. | |
| 7,749,194 B2 | 7/2010 | Edwards et al. | |
| 7,753,879 B2 | 7/2010 | Mernoe | |
| 7,766,873 B2 | 8/2010 | Moberg et al. | |
| 7,776,030 B2 | 8/2010 | Estes et al. | |
| 7,780,636 B2 | 8/2010 | Radmer et al. | |
| 7,780,637 B2 | 8/2010 | Jerde et al. | |
| 7,789,857 B2 | 9/2010 | Moberg et al. | |
| 7,789,862 B2 | 9/2010 | Thorne, Jr. | |
| 7,801,599 B2 | 9/2010 | Young et al. | |
| 7,806,868 B2 | 10/2010 | De Polo et al. | |
| 7,815,622 B2 | 10/2010 | Istoc et al. | |
| 7,828,528 B2 | 11/2010 | Estes et al. | |
| 7,837,659 B2 | 11/2010 | Bush, Jr. et al. | |
| 7,846,132 B2 | 12/2010 | Gravesen et al. | |
| 7,857,131 B2 | 12/2010 | Vedrine | |
| 7,879,025 B2 | 2/2011 | Jacobson et al. | |
| 7,879,026 B2 | 2/2011 | Estes et al. | |
| 7,892,206 B2 | 2/2011 | Moberg et al. | |
| 7,918,825 B2 | 4/2011 | O'Connor et al. | |
| 7,918,843 B2 | 4/2011 | Genosar et al. | |
| 7,935,104 B2 | 5/2011 | Yodfat et al. | |

(56) References Cited

U.S. PATENT DOCUMENTS

| | | | |
|---|---|---|---|
| 7,935,105 | B2 | 5/2011 | Miller et al. |
| 7,938,803 | B2 | 5/2011 | Mernoe et al. |
| 7,955,305 | B2 | 6/2011 | Moberg et al. |
| 7,967,784 | B2 | 6/2011 | Pongpairochana et al. |
| 7,981,105 | B2 | 7/2011 | Adair et al. |
| 7,988,683 | B2 | 8/2011 | Adair et al. |
| 7,993,300 | B2 | 8/2011 | Nyholm et al. |
| 7,998,111 | B2 | 8/2011 | Moberg et al. |
| 8,021,357 | B2 | 9/2011 | Tanaka et al. |
| 8,025,658 | B2 | 9/2011 | Chong et al. |
| 8,029,469 | B2 | 10/2011 | Ethelfeld |
| 8,034,019 | B2 | 10/2011 | Nair et al. |
| 8,038,666 | B2 | 10/2011 | Triplett et al. |
| 8,057,436 | B2 | 11/2011 | Causey et al. |
| 8,062,253 | B2 | 11/2011 | Nielsen et al. |
| 8,062,257 | B2 | 11/2011 | Moberg et al. |
| 8,065,096 | B2 | 11/2011 | Moberg et al. |
| 8,066,694 | B2 | 11/2011 | Wagener |
| D650,079 | S | 12/2011 | Presta et al. |
| D652,503 | S | 1/2012 | Cameron et al. |
| 8,105,279 | B2 | 1/2012 | Mernoe et al. |
| 8,114,046 | B2 | 2/2012 | Covino et al. |
| 8,114,064 | B2 | 2/2012 | Alferness et al. |
| 8,114,066 | B2 | 2/2012 | Naef et al. |
| 8,147,446 | B2 | 4/2012 | Yodfat et al. |
| 8,152,764 | B2 | 4/2012 | Istoc et al. |
| 8,152,770 | B2 | 4/2012 | Reid |
| 8,152,779 | B2 | 4/2012 | Cabiri |
| 8,152,793 | B2 | 4/2012 | Keinanen et al. |
| 8,157,693 | B2 | 4/2012 | Waksmundzki |
| 8,157,769 | B2 | 4/2012 | Cabiri |
| 8,162,923 | B2 | 4/2012 | Adams et al. |
| 8,167,841 | B2 | 5/2012 | Teisen-Simony et al. |
| 8,172,804 | B2 | 5/2012 | Bikovsky |
| 8,182,447 | B2 | 5/2012 | Moberg et al. |
| 8,182,462 | B2 | 5/2012 | Istoc et al. |
| 8,197,444 | B1 | 6/2012 | Bazargan et al. |
| 8,206,351 | B2 | 6/2012 | Sugimoto et al. |
| 8,267,893 | B2 | 9/2012 | Moberg et al. |
| 8,267,921 | B2 | 9/2012 | Yodfat et al. |
| 8,287,520 | B2 | 10/2012 | Drew et al. |
| 8,308,679 | B2 | 11/2012 | Hanson et al. |
| 8,348,898 | B2 | 1/2013 | Cabiri |
| 8,372,039 | B2 | 2/2013 | Mernoe et al. |
| 8,373,421 | B2 | 2/2013 | Lindegger et al. |
| 8,409,142 | B2 | 4/2013 | Causey et al. |
| 8,414,557 | B2 | 4/2013 | Istoc et al. |
| 8,430,847 | B2 | 4/2013 | Mernoe et al. |
| 8,469,942 | B2 | 6/2013 | Kow et al. |
| 8,474,332 | B2 | 7/2013 | Bente, IV et al. |
| 8,475,408 | B2 | 7/2013 | Mernoe et al. |
| 8,479,595 | B2 | 7/2013 | Vazquez et al. |
| 8,483,980 | B2 | 7/2013 | Moberg et al. |
| 8,495,918 | B2 | 7/2013 | Bazargan et al. |
| 8,512,287 | B2 | 8/2013 | Cindrich et al. |
| 8,517,987 | B2 | 8/2013 | Istoc et al. |
| 8,523,803 | B1 | 9/2013 | Favreau |
| 8,556,856 | B2 | 10/2013 | Bazargan et al. |
| 8,574,216 | B2 | 11/2013 | Istoc et al. |
| 8,603,026 | B2 | 12/2013 | Favreau |
| 8,603,027 | B2 | 12/2013 | Favreau |
| 8,617,110 | B2 | 12/2013 | Moberg et al. |
| 8,628,510 | B2 | 1/2014 | Bazargan et al. |
| 8,647,074 | B2 | 2/2014 | Moberg et al. |
| 8,647,296 | B2 | 2/2014 | Moberg et al. |
| 8,668,672 | B2 | 3/2014 | Moberg et al. |
| 8,674,288 | B2 | 3/2014 | Hanson et al. |
| 8,679,060 | B2 | 3/2014 | Mernoe et al. |
| 8,681,010 | B2 | 3/2014 | Moberg et al. |
| 8,690,855 | B2 | 4/2014 | Alderete, Jr. et al. |
| 8,708,961 | B2 | 4/2014 | Field et al. |
| 8,751,237 | B2 | 6/2014 | Kubota |
| 8,753,326 | B2 | 6/2014 | Chong et al. |
| 8,753,331 | B2 | 6/2014 | Murphy |
| 8,764,707 | B2 | 7/2014 | Moberg et al. |
| 8,764,723 | B2 | 7/2014 | Chong et al. |
| 8,771,222 | B2 | 7/2014 | Kanderian, Jr. et al. |
| 8,777,896 | B2 | 7/2014 | Starkweather et al. |
| 8,777,924 | B2 | 7/2014 | Kanderian, Jr. et al. |
| 8,777,925 | B2 | 7/2014 | Patton |
| 8,784,369 | B2 | 7/2014 | Starkweather et al. |
| 8,784,370 | B2 | 7/2014 | Lebel et al. |
| 8,790,295 | B1 | 7/2014 | Sigg et al. |
| 8,795,224 | B2 | 8/2014 | Starkweather et al. |
| 8,795,231 | B2 | 8/2014 | Chong et al. |
| 8,795,260 | B2 | 8/2014 | Drew |
| 8,801,668 | B2 | 8/2014 | Ali et al. |
| 8,810,394 | B2 | 8/2014 | Kalpin |
| 9,463,280 | B2 | 10/2016 | Cabiri |
| 2002/0040208 | A1 | 4/2002 | Flaherty et al. |
| 2002/0043951 | A1 | 4/2002 | Moberg |
| 2002/0055711 | A1 | 5/2002 | Lavi et al. |
| 2003/0135159 | A1 | 7/2003 | Daily et al. |
| 2003/0160683 | A1 | 8/2003 | Blomquist |
| 2003/0171717 | A1 | 9/2003 | Farrugia et al. |
| 2003/0199825 | A1 | 10/2003 | Flaherty |
| 2004/0085215 | A1 | 5/2004 | Moberg et al. |
| 2004/0092873 | A1 | 5/2004 | Moberg |
| 2004/0116866 | A1 | 6/2004 | Gorman et al. |
| 2004/0260233 | A1 | 12/2004 | Garibotto et al. |
| 2005/0065472 | A1 | 3/2005 | Cindrich et al. |
| 2005/0070845 | A1 | 3/2005 | Faries et al. |
| 2005/0071487 | A1 | 3/2005 | Lu et al. |
| 2005/0171512 | A1 | 8/2005 | Flaherty |
| 2005/0177136 | A1 | 8/2005 | Miller |
| 2005/0197650 | A1 | 9/2005 | Sugimoto et al. |
| 2005/0238507 | A1 | 10/2005 | Dilanni et al. |
| 2005/0258714 | A1 | 11/2005 | Henderson et al. |
| 2006/0095014 | A1 | 5/2006 | Ethelfeld |
| 2006/0122577 | A1 | 6/2006 | Poulsen et al. |
| 2006/0173408 | A1 | 8/2006 | Wyrick |
| 2006/0173439 | A1 | 8/2006 | Thorne et al. |
| 2006/0184154 | A1 | 8/2006 | Moberg et al. |
| 2006/0229569 | A1 | 10/2006 | Lavi et al. |
| 2006/0264890 | A1 | 11/2006 | Moberg et al. |
| 2006/0283465 | A1 | 12/2006 | Nickel et al. |
| 2007/0021733 | A1 | 1/2007 | Hansen et al. |
| 2007/0049865 | A1 | 3/2007 | Radmer et al. |
| 2007/0118405 | A1 | 5/2007 | Campbell et al. |
| 2007/0149926 | A1 | 6/2007 | Moberg et al. |
| 2007/0167912 | A1 | 7/2007 | Causey et al. |
| 2007/0191770 | A1 | 8/2007 | Moberg et al. |
| 2007/0219480 | A1 | 9/2007 | Kamen et al. |
| 2007/0282269 | A1 | 12/2007 | Carter et al. |
| 2008/0033369 | A1 | 2/2008 | Kohlbrenner et al. |
| 2008/0051710 | A1 | 2/2008 | Moberg et al. |
| 2008/0051711 | A1 | 2/2008 | Mounce et al. |
| 2008/0051727 | A1 | 2/2008 | Moberg et al. |
| 2008/0059133 | A1 | 3/2008 | Edwards et al. |
| 2008/0125700 | A1 | 5/2008 | Moberg et al. |
| 2008/0140006 | A1 | 6/2008 | Eskuri et al. |
| 2008/0140018 | A1 | 6/2008 | Enggaard et al. |
| 2008/0147004 | A1 | 6/2008 | Mann et al. |
| 2008/0156476 | A1* | 7/2008 | Smisson ............... A61M 5/44 165/185 |
| 2008/0167641 | A1 | 7/2008 | Hansen et al. |
| 2008/0188813 | A1 | 8/2008 | Miller et al. |
| 2008/0215006 | A1 | 9/2008 | Thorkild |
| 2008/0221522 | A1 | 9/2008 | Moberg et al. |
| 2008/0221523 | A1 | 9/2008 | Moberg et al. |
| 2008/0269723 | A1 | 10/2008 | Mastrototaro et al. |
| 2008/0294143 | A1 | 11/2008 | Tanaka et al. |
| 2008/0306449 | A1 | 12/2008 | Kristensen et al. |
| 2008/0312601 | A1 | 12/2008 | Cane |
| 2008/0319416 | A1 | 12/2008 | Yodfat et al. |
| 2009/0054750 | A1 | 2/2009 | Jennewine |
| 2009/0076453 | A1 | 3/2009 | Mejlhede et al. |
| 2009/0088694 | A1 | 4/2009 | Carter et al. |
| 2009/0088731 | A1 | 4/2009 | Campbell et al. |
| 2009/0093792 | A1 | 4/2009 | Gross et al. |
| 2009/0093793 | A1 | 4/2009 | Gross et al. |
| 2009/0124977 | A1 | 5/2009 | Jensen |
| 2009/0149830 | A1 | 6/2009 | Spector |
| 2009/0182277 | A1 | 7/2009 | Carter |

(56) References Cited

U.S. PATENT DOCUMENTS

| | | |
|---|---|---|
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0276411 A1 | 11/2010 | Hansen et al. |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0060284 A1* | 3/2011 | Harr .............. A61M 5/14244 604/153 |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0184342 A1 | 7/2011 | Pesach et al. |
| 2011/0201998 A1 | 8/2011 | Pongpairochana et al. |
| 2011/0224614 A1 | 9/2011 | Moberg et al. |
| 2011/0233393 A1 | 9/2011 | Hanson et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0313351 A1 | 12/2011 | Kamen et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0310153 A1 | 12/2012 | Moberg et al. |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0175192 A1 | 7/2013 | Iio et al. |
| 2013/0218089 A1 | 8/2013 | Davies et al. |
| 2013/0218092 A1 | 8/2013 | Davies et al. |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0171881 A1 | 6/2014 | Cabiri |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0210631 A1 | 7/2014 | Zavis |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |
| 2014/0288511 A1 | 9/2014 | Tan-Malecki et al. |
| 2015/0011976 A1 | 1/2015 | Vouillamoz et al. |
| 2016/0015910 A1 | 1/2016 | Mukai et al. |

FOREIGN PATENT DOCUMENTS

| | | |
|---|---|---|
| EP | 0744975 A1 | 12/1996 |
| EP | 1666080 A1 | 6/2006 |
| EP | 2060606 A1 | 5/2009 |
| EP | 2345441 A1 | 7/2011 |
| EP | 2454483 B1 | 8/2015 |
| WO | 8911302 A1 | 11/1989 |
| WO | 9009202 A1 | 8/1990 |
| WO | 9521645 A1 | 8/1995 |
| WO | 9632975 A1 | 10/1996 |
| WO | 9721457 A1 | 6/1997 |
| WO | 9733638 A1 | 9/1997 |
| WO | 2007092618 A2 | 8/2007 |
| WO | 2007130868 A1 | 11/2007 |
| WO | 2008024810 A2 | 2/2008 |
| WO | 2008024814 A2 | 2/2008 |
| WO | 2008129549 A1 | 10/2008 |
| WO | 2009081262 A1 | 7/2009 |
| WO | 2011090955 A1 | 7/2011 |
| WO | 2011113806 A1 | 9/2011 |
| WO | 2012032411 A2 | 3/2012 |

OTHER PUBLICATIONS

Office Action dated Oct. 28, 2015 in U.S. Appl. No. 13/429,942 by Cabiri.
Office Action dated Jan. 5, 2016 in U.S. Appl. No. 14/696,644 by Cabiri.
Office Action dated Dec. 3, 2015 in CN Application No. 201280068544.0.
U.S. Appl. No. 14/683,253 by Cabiri, filed Apr. 10, 2015.
Office Action dated May 18, 2015 in U.S. Appl. No. 13/429,942 by Cabiri.

(56) References Cited

OTHER PUBLICATIONS

Office Action dated Jan. 28, 2015 in U.S. Appl. No. 13/429,942 by Cabiri.
U.S. Appl. No. 14/593,041 by Cabiri, filed Jan. 9, 2015.
Int'l Search Report and Written Opinion dated Aug. 28, 2014 in Int'l Application No. PCT/US2014/035662.
Int'l Preliminary Report on Patentability dated Aug. 14, 2014 in Int'l Application No. PCT/US2012/050696.
U.S. Appl. No. 14/372,384 by Cabiri, filed Jul. 15, 2014.
Office Action dated Aug. 15, 2013 in U.S. Appl. No. 13/429,942 by Cabiri.
Int'l Search Report and Written Opinion dated Jun. 30, 2014 in Int'l Application No. PCT/US2013/031598.
U.S. Appl. No. 13/429,942 by Cabiri, filed Mar. 26, 2012.
Int'l Search Report and Written Opinion dated Apr. 5, 2013 in Int'l Application No. PCT/US2012/050696.
Office Action dated Feb. 24, 2016 in U.S. Appl. No. 13/429,942 by Cabiri.
Office Action dated Jan. 16, 2014 in U.S. Appl. No. 13/429,942 by Cabiri.
Office Action dated Apr. 19, 2016 in U.S. Appl. No. 14/372,384, by Cabiri.
Office Action dated Jun. 1, 2016 in CN Application No. 2013800274556.
Office Action dated Jun. 17, 2016 in CN Application No. 201280068544.0.
Office Action dated Jul. 29, 2016 in U.S. Appl. No. 14/696,644, by Cabiri.
Office Action dated Nov. 9, 2016 in U.S. Appl. No. 14/683,253, by Cabiri.

* cited by examiner

SENSING A STATUS OF AN INFUSER BASED ON SENSING MOTOR CONTROL AND POWER INPUT

BACKGROUND OF THE INVENTION

The present invention, in some embodiments thereof, relates to a system and method to monitor drug infusion to a patient and, more particularly, but not exclusively, to a system and method to monitor the status of a portable battery operated infuser through monitoring a power input and/or control of a drive mechanism.

U.S. Pat. No. 6,830,558 discloses a device for delivering fluid to a patient including an exit port assembly adapted to connect to a transcutaneous patient access tool, a flow path extending from the exit port assembly, and a flow condition sensor assembly. The sensor assembly includes a resilient diaphragm having a first surface positioned against the flow path, a chamber wall defining a sensor chamber adjacent a second surface of the diaphragm, and at least one sensor arranged to provide a threshold signal when the second surface of the diaphragm expands into the chamber in response to at least one predetermined fluid flow condition occurring in the flow path. The sensor includes a first electrode secured on the diaphragm, a second electrode positioned in a fixed location with respect to the first electrode, and an impedance meter connected between the electrodes.

U.S. Pat. No. 7,828,528 discloses an occlusion sensor system for an infusion pump system that communicates with control circuitry to detect the presence of an occlusion. In some embodiments, the occlusion sensor system includes first components that are located within a disposable and non-reusable pump device, and second components that are located within a reusable controller device, the second components being in operable communication with the first components to determine whether a fluid is flowing from the pump device.

U.S. Pat. No. 7,122,982 discloses a rotation information detection device detecting rotation information of a DC motor based on a surge component waveform superimposed on a voltage waveform between the terminals of the DC motor or a current waveform of the DC motor. A circuit is provided which supplies a current of a current value Ipwm 45% during motor forward rotation or Ipwm 55% during reverse motor rotation to the motor over the period from when the motor starts braking operation to when it stops.

U.S. Pat. No. 7,692,399 discloses a method of controlling a DC motor is presented. In a determining action, a thermal power dissipation is determined from a motor input and a motor velocity. In another determining action, a motor temperature is determined based on a thermal model using the thermal power dissipation. In an adjusting action, a usage of the motor is adjusted, taking the motor temperature into account.

International Patent Application No. PCT/US12/66036 discloses a system that may regulate voltage supplied from a power source to an integrated circuit and/or an inertial device. A minimal voltage may be maintained in the integrated circuit by temporarily cutting off current to the inertial device to supply surges of voltage to the controller. Optionally voltage may be smoothed between said surges for example by adding capacitance and/or a current restrictor.

SUMMARY OF THE INVENTION

According to an aspect of some embodiments of the present invention there is provided a method of determining a status of a battery operated drug infusing device including: controlling the device based on a performance of the device; measuring an input parameter of the device, and ascertaining a status of the device dependent on both a magnitude of the input parameter and the controlling.

According to some embodiments of the invention, the performance of the device includes a cumulative movement of the device and the controlling includes limiting a time of current input to the device and the measuring includes measuring a magnitude of the current input to the device over time and the ascertaining includes combining the magnitude and the time of the current input to the device to determine a combined measure and wherein the ascertaining is based on a value of the combined measure.

According to some embodiments of the invention, the cumulative movement includes a number of revolutions during a time period.

According to some embodiments of the invention, the limiting includes limiting a pulse density of the current input in the time period.

According to some embodiments of the invention, the combined measure includes a product of the current magnitude over the time.

According to some embodiments of the invention, the controlling affects the input parameter.

According to some embodiments of the invention, a result of the measuring serves as a proxy for a parameter of the controlling.

According to some embodiments of the invention, a time dependence of the measured input parameter serves as the proxy for the parameter of the controlling.

According to some embodiments of the invention, the ascertaining includes determining a combined measure of the input parameter magnitude over time.

According to some embodiments of the invention, the combined measure includes a product of the input parameter magnitude and the time.

According to some embodiments of the invention, the controlling includes pulse density modulation and the ascertaining depends on the pulse density.

According to some embodiments of the invention, the controlling includes a feedback loop.

According to some embodiments of the invention, the controlling includes a negative feedback loop.

According to some embodiments of the invention, the status includes at least one element selected from the group consisting of, a blockage, a disengagement, changing of an active mechanical part, discharging medicine, and not discharging.

According to some embodiments of the invention, the input parameter is magnitude of current and the controlling includes counting a number of rotations wherein the number of rotations is proportional to a cumulative discharge of the device, and cutting off the current when the number reaches a threshold.

According to some embodiments of the invention, a rate of the counting is less than four times a sampling rate of the measuring.

According to some embodiments of the invention, the input parameter is unregulated.

According to some embodiments of the invention, the controlling includes temporarily cutting off the input parameter.

According to an aspect of some embodiments of the present invention there is provided a drug infusion device including: a DC power source; an actuator; a performance sensor operationally coupled to an output of the actuator; a controller which adjusts a power input of the actuator according to an output of the performance sensor; an input sensor operationally coupled to the power input; a processor which ascertains the status of the device dependent on the adjusting based on an output of the sensor.

According to some embodiments of the invention, the performance sensor includes a revolution counter.

According to some embodiments of the invention, the actuator includes a DC motor.

According to some embodiments of the invention, the drug infusion device further includes a pulse density circuit, and wherein the adjusting is by pulse density modulation.

According to some embodiments of the invention, the sensor is a current sensor and the power input includes a current.

According to some embodiments of the invention, the processor computes an product of a magnitude of the current over time and wherein the ascertaining is dependent on the product.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a key board or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
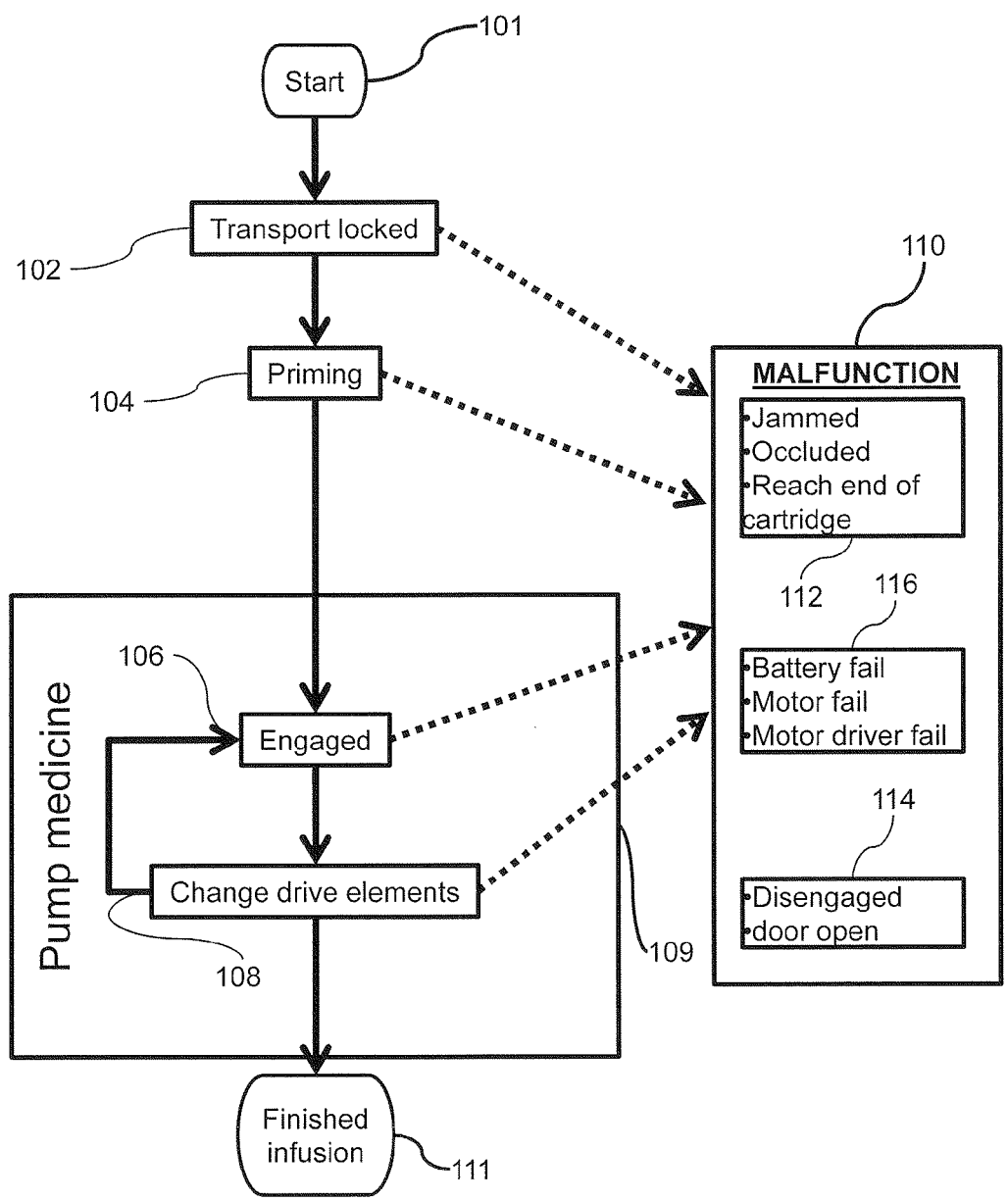
FIG. 1 is a state chart of statuses of a patch injector, in accordance with an exemplary embodiment of the invention.

The present invention, in some embodiments thereof, relates to a system and method to monitor drug infusion to a patient and, more particularly, but not exclusively, to a system and method to monitor the status of a portable battery operated infuser through monitoring a power input and/or a control of a drive mechanism.

Overview

An aspect of some embodiments of the current invention includes determining the status of a medical infuser from multiple factors in motor power input and/or control mode. Optionally, a simple proxy measurement may be used in lieu of measuring motor performance. For example, integrating input current to the motor over time may be used to determine an input parameter (for example input current) and/or a control mode (for example pulse density) which may be dependent on a performance parameter (for example motor speed).

In some embodiments, measurements may be adjusted according to control parameters of the motor (for example measurements may be synchronized with power pulses to the motor) and/or measurement values may be deduced based on known control parameters of the motor (for example, measurements may be skipped when power is cut off to the motor and measurement values deduced based on the known control parameter [lack of input power]). Input levels may be compared to fixed threshold values, dynamic threshold values and/or or a differential measure may be computed. Changes may optionally be analyzed based on a logic structure that includes the expected status changes and/or or the expected time between statuses and/or the expected variability of values.

An aspect of some embodiments of the present invention relates to a system and method for determining a status of a portable infuser in the presence of confounding factors. For example, motor control of an infuser may include a negative feedback loop. For example the negative feedback loop may complicate determination of motor status based on a measured magnitude of the input parameter. In some embodiments knowledge of the control mode of the motor may be combined with a simple measurement the input parameter to determine the status of a complex system. The control mode optionally may be determined based on motor input and/or performance parameters. For example, the control mode may be determined from the time dependence of measurements of a controlled input parameter.

In some embodiments, the method of the current invention may be used to determine the loads status of a motor. For example motor output may be controlled by pulse density modulation, optionally employing a negative feedback loop to preserve performance over changing conditions. Changes in pulse density may complicate detection of changes of load using convention monitoring techniques (for instance based on input current to the motor). Optionally by combining a measured parameter (for example time dependence of an input current level) with a control mode (for example pulse width) the load may be determined under complex control conditions. Optionally, the control mode (for example pulse width) may be deduced from the measured input current. Optionally, input current measurements may be synchronized to motor input pulses. In some embodiments, motor performance and/or infuser status may be deduced without requiring direct measurements of physical outcomes (for example pressures, force, torque, speed etc.).

Proper motor control and status detection may optionally increase the shelf life a device, allow the use of cheaper and/or smaller components, increase convenience, decrease need for supervision and/or increase reliability.

Infuser Status

An aspect of some embodiments of the instant invention relates to determining a status of an infuser, in accordance with an exemplary embodiment of the invention. For example a portable infuser may include a patch injector and/or a home treatment device and/or a battery operated device. For example, an infuser may include SmartDose® Electronic Patch Injector System being developed by Medimop Medical Projects Ltd., a subsidiary of West Pharmaceutical Services, Inc.

For example statuses that may be detected may include one or more of: stages of normal operating for example, overcoming a transport lock, priming the system (for example puncturing a septum and/or disengagement while overcoming a preliminary gap), beginning of medicine discharge, changes of a drive element and/or reaching the end of the cartridge and/or reaching the end of the extension mechanism; a malfunction causing disengagement for example an open access door, a screw thread disengaged, a gear disengaged; and/or a malfunction causing increased resistance, for example an occlusion, a jam; and/or a malfunction of a component for example a battery failure, a motor failure and/or a motor driver failure.

Determining Factors

In some embodiments status determination may be deduced based on one or more factors of performance including, for example—rotational speed, number of rotations, motor input current, motor input voltage, pulse density, energy input, and/or time dependence of the above.

An aspect of some embodiments of the current invention relates to determining the status of an infuser and/or performance factors without direct measurement. For example temperature and/or flow rate and/or pressure and or speed may be deduced from a surrogate measurement. Optionally a surrogate measurement may include current, voltage and/or changes over time.

In some embodiments, performance of an infuser is controlled. Control may optionally include a feedback loop. Control may be based on a course assessment of performance. For example, infuser discharge may be controlled based on a coarse rotational counter. The status of the infuser may be from measurements of a controlled input parameter (for example the input current over time). Ascertaining the status may account for performance factors based on the relationship between the measured input and the control scheme of the infuser. In some embodiments, the rate of injection is controlled by turning on or off the motor. Optionally the motor speed may not be regulated and/or measured (and/or may only be known imprecisely, for example based on the counted number of revolutions in a time period). The motor speed may be an unregulated result of the load and/or voltage input and/or motor properties (which may not be known and/or measured precisely).

Confounding Factors

In some embodiments, calculations of infuser status may account for various confounding factors including for example a feedback loop that that achieves an injection volume, a regulation scheme preserving voltage input to a CPU, variability in component performance (for example battery performance and/or motor performance) variations in flow resistance of components (for example of a hypodermic needle and/or of tubing), variation in friction (for example of extension rods and/or a plunger), variations in temperature, variations in viscosity.

For example a patch injector may pump a medicine with dynamic viscosity ranging between for example 2 cp to 15 cp. The temperature of infuser components (for example a battery and/or the medicine) may range between −5° C. to 45° C. Performance of a motor may vary as much as 30% or even as much as 40% from a rated value (for example of output power, torque and/or speed). The injector may be used to inject a dose of for example between 1 ml to 5 ml of medicine. The injection may continue over a period of for example between 5 minutes to 24 hours. Optionally, power may be supplied by batteries, for example standard Silver Oxide (Ag2O) batteries and/or lithium batteries.

In some embodiments, medicine may be administered by repeated small pulses. For example, a controller may drive a the motor for a 300 msec dosage period, measure the number of rotations, compute the quantity injected and determine a waiting time for next dosage in order to meet a stored injection rate and then wait and afterwards inject again for 300 msec. For some delivery rates, the waiting period between doses may for example range between 500 msec to 5 sec. For lower delivery rates the waiting period may range between 3 sec and 5 minutes. In some embodiments the number of revolution in a pulse period may be fixed and the time of the pulse may vary, for example between 100 and 900 msec. In the waiting period, the injector may be in a sleep mode. For example, in the sleep mode the controller may remain active, measuring time until the next dosage and remembering the delivery parameters, but the motor and/or sensors may be inactive. In some embodiments, the pulse density modulation motor control may have a duty cycle ranging between 2% and 20%. In some embodiments a component of an infuser may be driven beyond a rated capacity. For example a component may be driven from 150% to 3000% or optionally from 30000% to 5000% of its rated capacity. For example a battery rated at 5 mA may be driven between 100 and 200 mA. Under such conditions, battery performance may degrade over time and/or depend on the pulse width modulation duty cycle. Changes in battery performance may, for example, cause changes in input voltage and/or current. Such changes may further complicate detection of the infuser mode, for example, based on current measurements.

Exemplary Detailed Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates some of the various statuses that may be distinguished in a medical infuser. A logic device may be supplied to determine the current status of the injector based on limited input data. The logic device may track status of the infuser, consider likely changes of status and consider alternative explanations of motor inputs and/or motor performance and/or changes thereof. Optionally, detected status can include a normal stage of injection (an embodiment may include one, some or all of the following statuses) for example transport locked 102, priming 104, pumping medicine 109, engaged 106, and/or changing a driving element 108. Optionally, detected status can include a malfunction for example a jam, an occlusion, rotational slippage, access door open etc.

In some embodiments, the controller may have an internal state machine including for example a state indicator. Optionally, interpretation of measured parameters may depend on the current state of the state machine. For example a sharp reduction of resistance before the beginning of medicine discharge may be interpreted as a normal priming state. For example a sharp reduction of resistance during medicine discharge may be interpreted as a disengagement malfunction. For example, a sharp increase in resistance during medicine discharge may be interpreted as a malfunction due to an occlusion. For example, a sharp increase in resistance at the end of medicine discharge may be interpreted as a plunger reaching the end of the cartridge. The controller may be programmed to issue a malfunction warning, take corrective action (for example wait and resume and/or change a discharge mode [for example higher or lower pulse density and/or discharge rate]) based on the detected status.

For example, when an infuser is activated 101, it may be in a transport locked 102 status. In the transport locked 102 status there may optionally be a medium resistance to motor movement due to a transport lock to prevent unintentional movement of the infuser drive train during transport and handling prior to use. In some embodiments, the infuser may leave the transport locked 102 status after a small movement of the drive train. Alternatively or additionally, the infuser may not have a transport lock and/or the drive train may have moved out of transport locked 102 status before activation of the infuser. For example, an infuser may start immediately in a priming 104 status and/or an engaged 106 status.

In some embodiments, in priming 104 status there may be a minimal resistance to movement of the drive train. Optionally, the infuser will remain in the priming 104 status only for a small range of movement of the drive chain. For example, there may be a small empty space between a medicine cartridge drive train and a support and/or an actuator and priming 104 may occur while the drive train covers that space. Alternatively or additionally, the priming 104 steps may include, for example puncturing a septum. Alternatively or additionally, in some embodiments the priming 104 stage may be lacking. For example an infuser may go straight from the transport locked 102 status to an engaged 106 status and/or may start in the engaged 106 status.

Once past optional preliminary statuses (for example transport locked 102 and/or priming 106) an infuser may begin pumping 109 a medicine. During pumping 109 the drive train may be engaged 106 to an actuator (for example a syringe plunger). For example, movement of the drive train may drive the actuator to pump 109 the drug into the patient.

In some embodiments, a drive train may include multiple drive elements. For example, the drive train may include a telescoping assembly pushing a plunger. The telescoping assembly may include one or more threaded rods as drive elements. During pumping the drive chain may switch between active rods. The threading of rods may be adjusted such that the relationship between discharge and rotations remains the same for more than one rod and/or different drive rods may have a different rotation to discharge relationship. Alternatively or additionally a drive train may include other elements such as gears and/or a piston.

In some embodiments, during pumping 109 a drive train may switch 108 driving elements. Switching may optionally be associated with a transient and/or continuous change in a. For example, a rod with a higher discharge to revolution ratio may produce a larger resistance to movement. Alternatively or additionally, even when two rods have the same revolutions to discharge ratio, there may be a different resistance to driving. For example a larger diameter rod may require more torque to move due to friction resistance and/or rods of different materials and/or geometries may have different resistances.

A detected state may include a malfunction 110. A malfunction may include for example an occlusion and/or a jammed part and/or a plunger reaching and end of its movement which may sometimes cause an increase 112 in resistance to movement. Alternatively or additionally a malfunction may include a disengagement of the drive train and/or a drive train failure (for example due to an open door and/or not inserting a cartridge and/or rotational slippage) which may result in a decrease 114 in resistance to movement. For example, if the door of an infuser is left open and/or a cartridge not inserted and/or a screw becomes disengaged, the drive train may move without engaging the actuator and/or if there is rotation slippage of a plunger and/or cartridge then a screw may spin without causing pumping of the medicine for example as referenced in U.S. Patent Publication No. 2009/0093792 which is incorporated herein by reference. In some cases, a malfunction may include other components 116 such a battery failure and/or motor failure and/or a motor driver failure. In fusion may finish 111 for example when a prescribed quantity of medicine has been discharged.

Exemplary Changes in Input Current for a Simple Infuser

Figure 2:
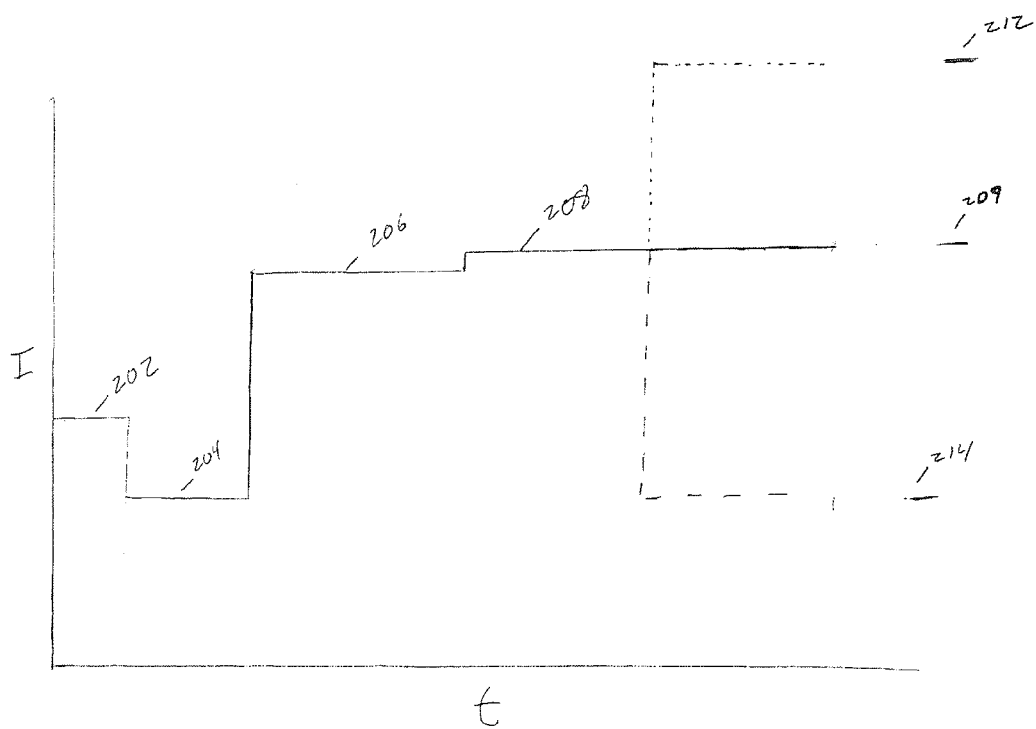
FIG. 2 is a schematic diagram of current vs. time for a direct powered patch injector, in accordance with an exemplary embodiment of the invention.

In some embodiments, there may be a simple relationship between input current and infuser status. For example, for a system with an optional steady voltage power source and an optional direct connection motor driver, resistance on the drive train may be directly related to the input current to the motor. FIG. 2 illustrates a schematic relationship between current and time (and changing infuser status) for an exemplary simple infuser system.

For example, when there is a small resistance to movement, for example while overcoming a transport lock 102, the input current to the motor may be low 202.

When the resistance to drive train movement is very low, for example when the infuser is in a priming 104 status, the input current may, for example, be very low 204.

When the resistance to drive train movement is high, for example, when the infuser is engaged 106 and/or pumping 109 medicine, the input current may be high 206.

When the resistance to drive train movement increases, for example when the drive train switches 108 to an increased friction drive element, the current may, for example, become higher 208.

Certain input currents may optionally be associated with malfunction 110 statuses. Interpretation of infuser status from current level may depend on the current state of the infuser. For example very high 212 current may be a sign of an occlusion or jam. The level of current that is defined as very high 212 may depend on the previous current level. For example, very high 212 current may be defined according to a relative change from a previous base line. For example very low 214 current may be a sign of disengagement of the drive train. Optionally, interpretation of very low 214 current levels may depend upon the status of the infuser. For example, during a priming 104 period, short drop in current levels may be interpreted as a normal part of priming 104. For example, during a pumping 109 period a drop in voltage may be interpreted as a malfunction 110. Continued high 209 input current after priming 104 may indicate proper functioning of an infuser during medicine pumping 109.

In some embodiments definitions of current levels may be adjusted, for example due to variability of components. For example variability in the voltage and/or internal resistance of a battery and/or of motor performance may change baseline behavior. Optionally, interpretation of very high, high, normal, low and/or very low current levels may be adjusted to account for baseline values. These values may change during operation (for example a battery voltage may and/or internal resistance may change over the infusion time).

A Method of Determining a Status of an Infuser

Figure 3:
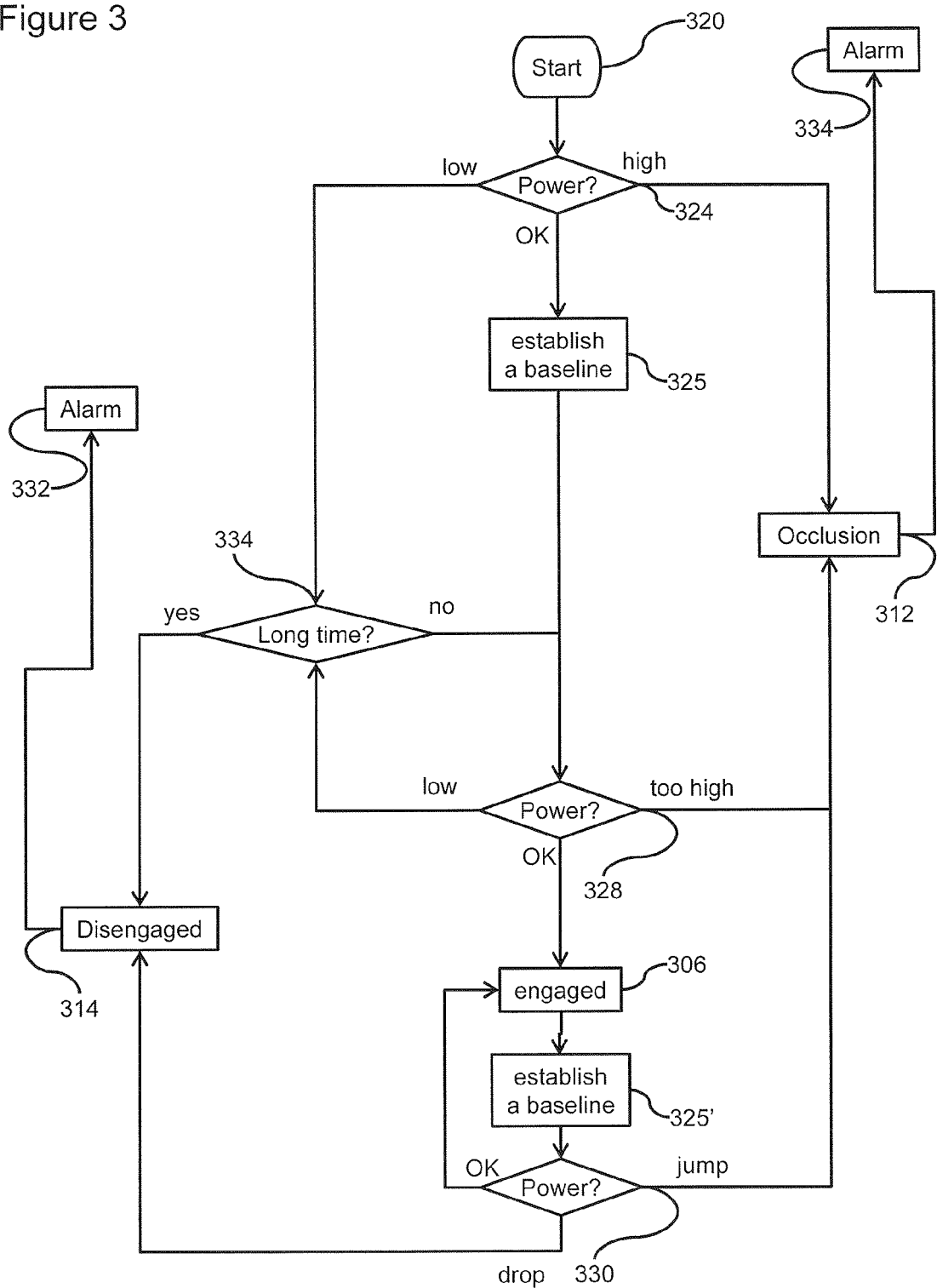
FIG. 3 is a flow chart illustrating determining a status of a patch injector, in accordance with an exemplary embodiment of the invention.

Referring now to the drawings, FIG. 3 illustrates a method of determining a status of an infuser from motor input and performance. The methodology can be understood with reference to the simple case of FIG. 2 with the input current being the indicator of power to the motor. In more complicated cases described herein below power to the motor may optionally include a more complex function that accounts for changes of input current over time and/or motor performance.

In some embodiments when an infuser is started 320, the input energy level is optionally compared 324 to a maximum and/or a minimum threshold. The input energy level may include, for example, the average input current measured in three samples over a for example between 100 and 500 mili-seconds (ms). If the input energy is above a maximum threshold, the infuser may be determined to be in a fault mode (for example, the maximum power level may be very high 212 input current level). Optionally, alarm may be set off 334 warning of a possible occlusion 312 status. If the energy input is below a minimum threshold (for example, very low 214 input current level), then the system may test 334 how long the low energy state continues. If the very low energy state continues only a short while (for example ranging between 100 ms to 60 sec.) the system may assume that the system was priming 204 and that there is no fault. If the low input energy level continues for a long time, a fault (for example that the system is improperly disengaged 314) may be determined and/or an alarm set off 332, for example warning of a possible disengagement of the power train.

In some embodiments, if the input energy is above a minimal threshold and below a maximum threshold, then it may be determined to be OK and established 325 as a baseline power level. If no fault has developed, the system may optionally continue to monitor 328 the input energy. If a high steady energy state develops, then the pump is determined to be engaged 306. A new baseline input energy may optionally be set 325'. From the beginning of the engaged status the system may count the number of revolutions of the motor. The medicine dosage applied may optionally be determined from the number of motor revolutions after engagement. For example each revolution of the motor may represent an injection volume of between $5 \times 10^{-4}$ to $5 \times 10^{-5}$ ml. The total discharge may for example range between 0.5 and 5 ml and/or the injection time may for example range for example between 5 minutes to 5 hours or in some cases to between 5 hours and 24 hours. For example the motor may revolve between $10^3$ and $5 \times 10^4$ revolutions during an injection (after it establishing engagement and/or discharge started until the end of injection.

If during the engaged status, the input energy drops or rises too much 330, the system may detect a fault in the injection and set off 332,334 a warning alarm for disengagement 314 and/or occlusion 312.

A More Complex Method of Motor Control

Figure 4:
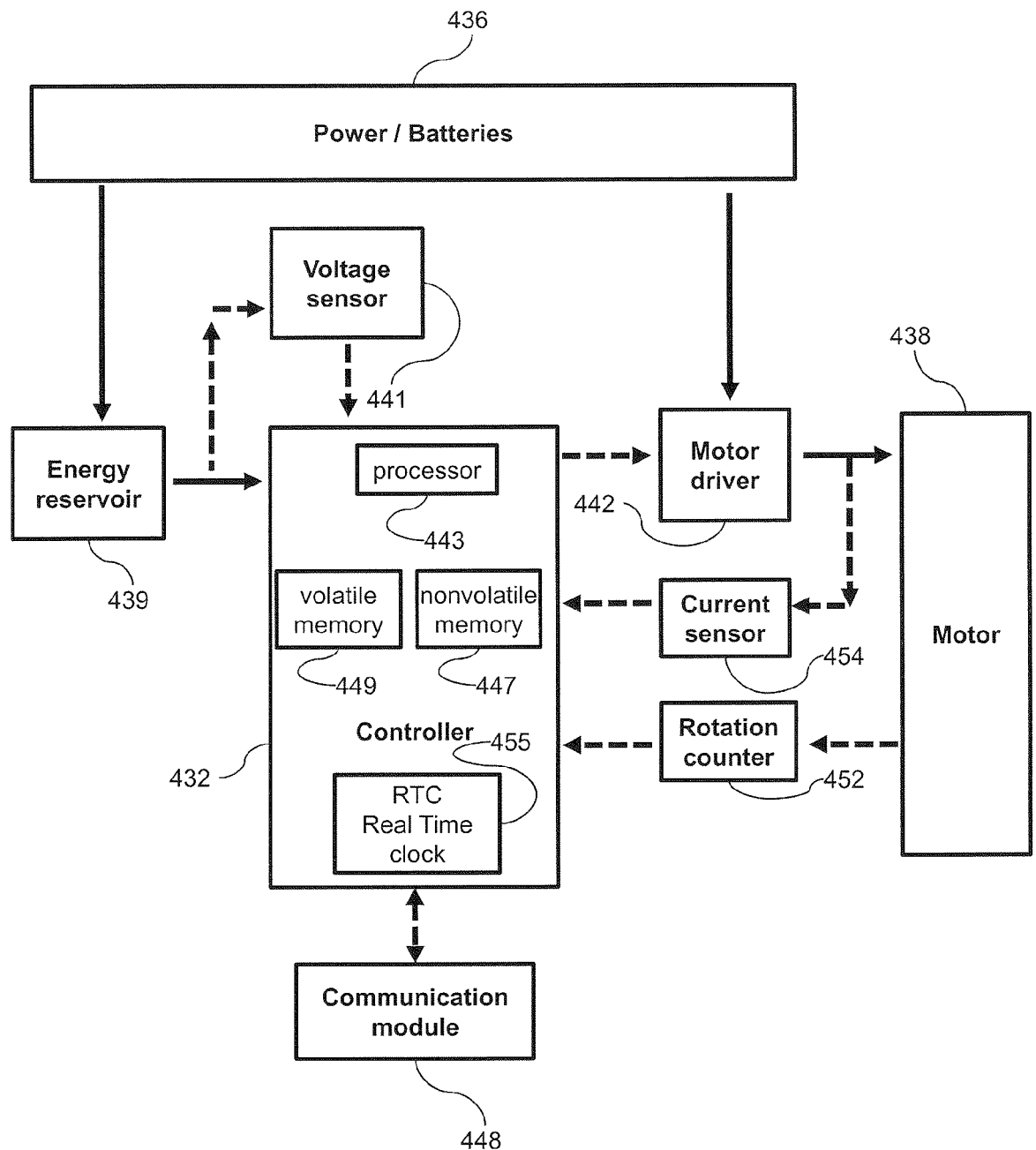
FIG. 4 is a schematic circuit diagram of a patch injector, in accordance with an exemplary embodiment of the invention.
Figure 5:
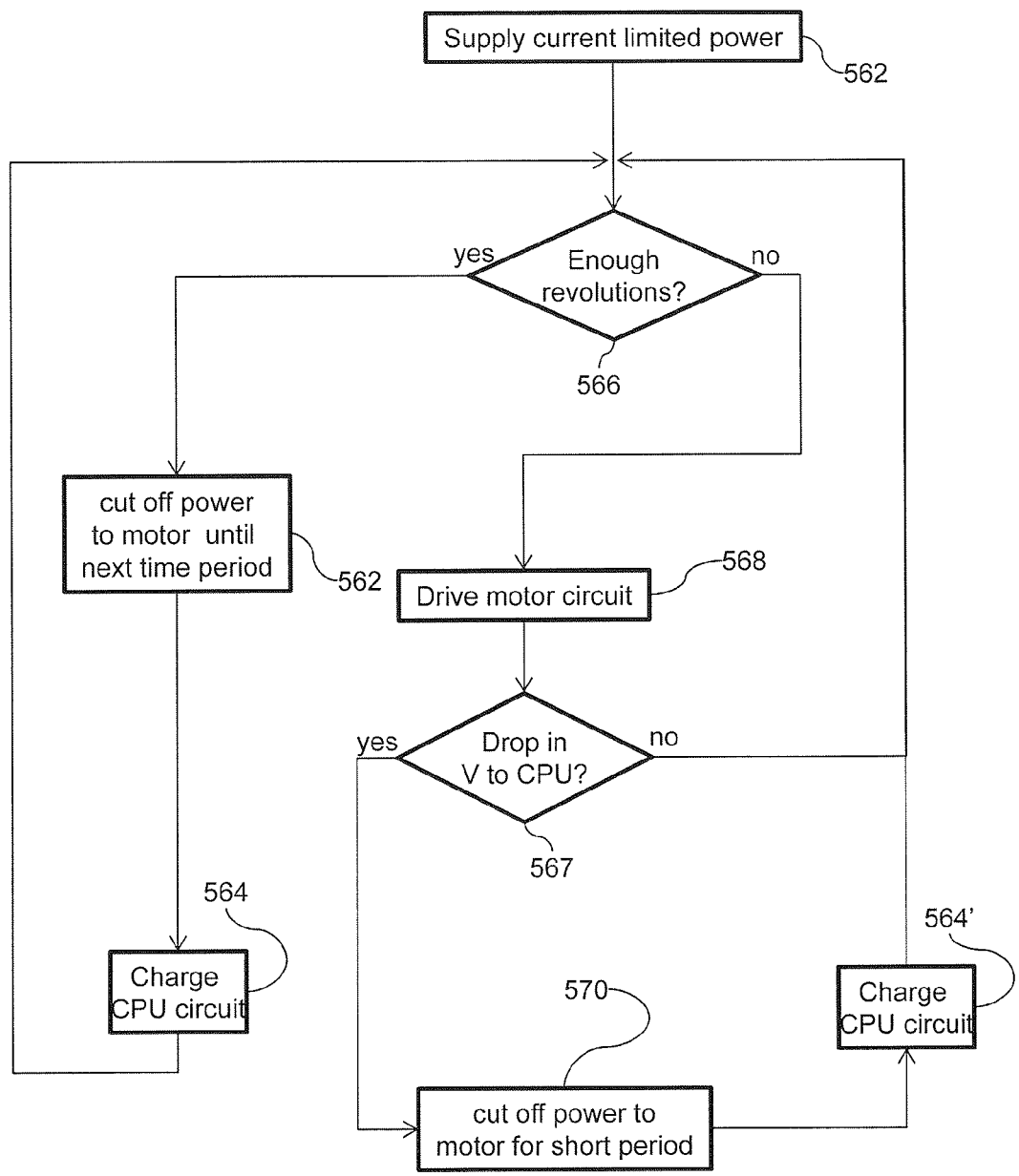
FIG. 5 is a is a flow chart illustrating control of a patch injector, in accordance with an exemplary embodiment of the invention.

FIGS. 4 and 5 are a circuit diagram and a flow chart illustration of an exemplary embodiment of a control method of a more complex disposable portable medical infusion pump. The exemplary infusion system may be designed to be cheap, disposable, small and/or reliable. Optionally, the system may include an actuator, for example a DC motor 438. DC motor may optionally draw a relatively high current. DC motor 438 may optionally drive a pump.

In some embodiments, the system may include a controller 432 including a processor 443. In some embodiments, controller may require a stable input voltage. In some embodiments, a cheap, small, and/or disposable power supply 436 (for example three Ag2O batteries) may supply 562 a current limited power. For example the batteries may not be able to simultaneously directly supply both the power requirement of the motor and the voltage requirements of the CPU. Optionally the infuser may include an electrical sensor (for example current sensor 454 and/or a voltage sensor 441) and or a motor performance sensor, (for example a rotation counter 452) to detect such changes in input energy and/or output performance of motor 438 and/or controller 432. Controller 432 may include, for example, a real time clock (RTC) 455. RTC 455 may be used, for example, to track time periods for motor pulses.

In some embodiments an energy reservoir 439 may supplied for controller 432. Optionally, the reservoir may supply a dependable voltage to the controller even when high current drawn by motor 438 causes the output voltage of power supply 436 to drop.

In the example of FIG. 4, optionally motor 438 drives a pump injecting a medication. The rate of injection is optionally controlled by controller 432. Exemplary embodiments of a control system for an infusion pump can be found in application U.S. provisional Ser. No. 61/592,978, on Jan. 31, 2012. A PCT application, PCT/US12/50696, claiming priority to this US provisional was filed on Aug. 14, 2012. Both applications are incorporated herein by reference.

In some embodiments, the length of injection and number of doses may be set and an adjustable pulse of power may be applied to the motor in each of a number of time periods to inject a determined dosage. For example, there may be a pulse every second that continues driving 568 motor 438. The pulse may continue until the motor has revolved a predetermined number of revolutions.

In some embodiments, controller 432 may include parameters for driving the motor in a non-volatile memory 447. Controller 432 may optionally direct motor driver 442 to apply pulses of power to the motor over predetermined time periods. For example in a given time period, controller 432 may determine 566 if motor 438 has completed the predetermined number of revolutions for the period. When the requisite number of revolutions has been completed power may be cut off 562 to motor 438. While power is cut off 562 to motor 438, energy reservoir 439 may be charged 564. Optionally, current in the pulses may be unregulated. Optionally, the precise rotational rate of the motor may be unmeasured.

In some embodiments, a motor may be connected to a pump such that each revolution of the motor injects a fixed quantity of medicine (for example 10-5 ml). For example, it may be desired to inject 3.5 ml over ten minutes. In the example, the desired injection rate may optionally be achieved by driving 568 motor 438 to revolve between 10 to 100 revolutions in a one second time period. For an injection that lasts five hours the motor time periods may be longer than one second (for example between 10 sec and 5 minutes and/or the number of revolutions in a time period may range between 3 and 30. For a 24 hour injection the length of a time period may range between 1 minute to 1 hour.

Optionally, the status indicators and/or the delivery parameters may be stored in a volatile memory 449. In some embodiments, it may be important that the controller not reset. For example, resetting may cause loss of parameter values stored in a volatile memory. For example, resetting of the controller may indicate a malfunction of the injector or cause a fault in the tracking of the injection, in some cases such a malfunction may for the patient to rush to the hospital or even endanger the patient's life.

In some embodiments, during the dosage period, the high current drawn by motor 432 may cause the voltage output of batteries 426 to drop below the reset threshold of controller 432. Optionally, upon detecting 567 a drop in voltage, reset of controller 432 may be avoided by cutting 570 power to motor 432 for a short period (for example less than the pulse time period and/or less than an inertial period of motor 432) during which time energy reservoir 439 may recharge 564'.

Optionally the infuser may include a communication module 448. Communication module 448 may include for example a communication cradle. Communication module 448 optionally be used, to program a delivery rate for a drug and/or to retrieve data on dosage and/or delivery conditions after the drug has been delivered. Optionally communication module 448 may also be used to adjust control parameters such as the length of a dosage period, the rate of current distribution. Communication module 448 may be used, for example, to warn a patient (for example via a warning light and/or a buzzer) of a malfunction and/or to warn a caretaker (for example a doctor and/or an emergency switchboard) of a malfunction, for example via a wireless network.

In some embodiments the infuser may include dynamic adjustment of operating parameters. For example, the infuser may be able to adjust itself to adapt to conditions or performance parts that may not be known a-priori. For example, if the infuser is stored for a long time batteries may not perform according to specifications. For example, if the infuser is used under cold conditions, the viscosity of the medicine may increase and the performance of batteries may be poor. In such a case, during a dosage period, motor 438 may draw higher than expected current. In such a case, during a dosage period, the drop of voltage output of battery may be more than expected. Dynamically adjusting operating parameters may include for example shortening pulse period and/or shortening the pulse length of the current distribution.

In some embodiments, the performance characteristics of the infuser may be adjusted for secondary reasons. For example the rate of pulses may be adjusted to achieve a desired vibration (patients may feel more confident that the device is working if they hear a reassuring humming sound).

In some embodiments, the voltage distribution cut off period may have a length of, for example, be between 2 and 50 msec. In some embodiments, the voltage distribution pulse to motor 438 may have a length of, for example, between 2 and 150 msec. In some embodiments, the duty cycle of the power distribution (pulses and cut offs) may range between 50% and 95%. In some embodiments, the pulse density modulation motor control may have a motor-on time ranging between 50 and 500 msec. In some embodiments, the pulse density modulation motor control may have a motor-off time ranging between 500 and 5000 msec. In some embodiments, the pulse density modulation motor control may have a duty cycle ranging between 2% and 20%.

In some embodiments, processor 443 may use outputs from rotation counter 452 and/or current sensor 454 and/or voltage sensor 441 to determine the status of the infuser. In some embodiments, rotation counter 452 may have a coarse resolution. For example the resolution of counter 452 may include full revolutions and/or half revolutions and/or quarter revolutions. For example the resolution of counter 452 may be too coarse to allow determination of changes motor speed on a time scale of sampling motor input measurements (for example the sample time scale of current sensor 454 and voltage sensor 441).

Exemplary Current Vs. Time for a More Complex Infuser

Figure 6:
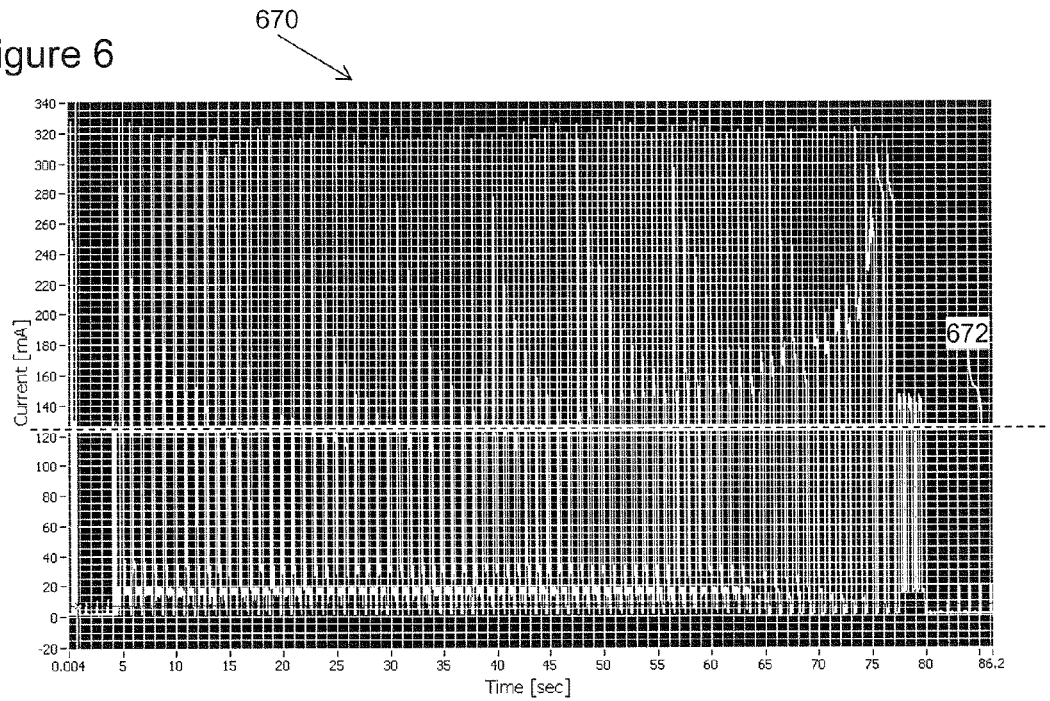
FIG. 6 is an experimental current vs. time graphs of a patch injector, in accordance with an exemplary embodiment of the invention.

FIG. 6 illustrates an experimental current vs. time graph 670 for an exemplary infuser wherein injection rate is being controlled by pulse width modulation (PWM). In exemplary graph 670 normal engaged pumping behavior is illustrated by times from 0 to 45 seconds. A baseline current level 672 of 125 mA is illustrated by the horizontal line. At 45 seconds a resistance was placed against the drive to simulate an occlusion. Starting at the occlusion time, 45 sec, the current value in graph 670 rises toward 280 mA.

The complex shape of graph 670 may make it difficult to reliably determine the baseline current value and/or deviations therefrom. For example, during normal operation (for example from 0 to 45 sec) each energy pulse jumps to a high current at the beginning of an energy pulse and then drops toward the baseline value. Slight changes in sampling time with respect to the pulse timing may make the current appear to be changing even when the infuser status has not changed. This behavior may be further complicated if short term pulse cut offs are added (for example as described above to preserve controller voltage).

Exemplary Indicator Integrating Changes in Pulse Width and Current

Figure 7A:
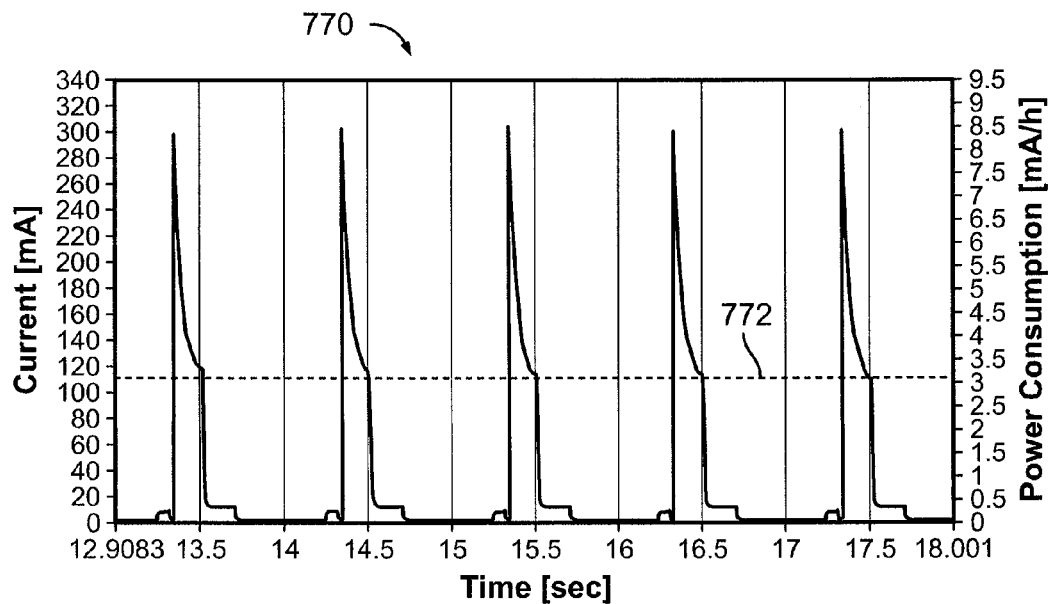
FIG. 7A, B, C are expanded experimental current vs. time graphs of a patch injector, in accordance with an exemplary embodiment of the invention.
Figure 7B:
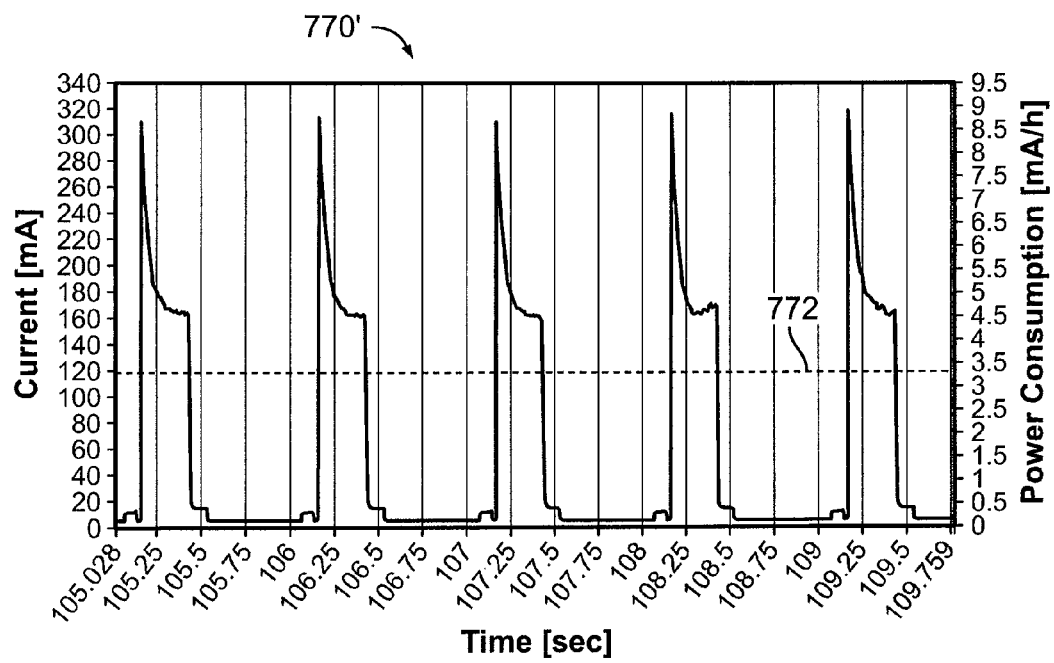
Figure 7C:
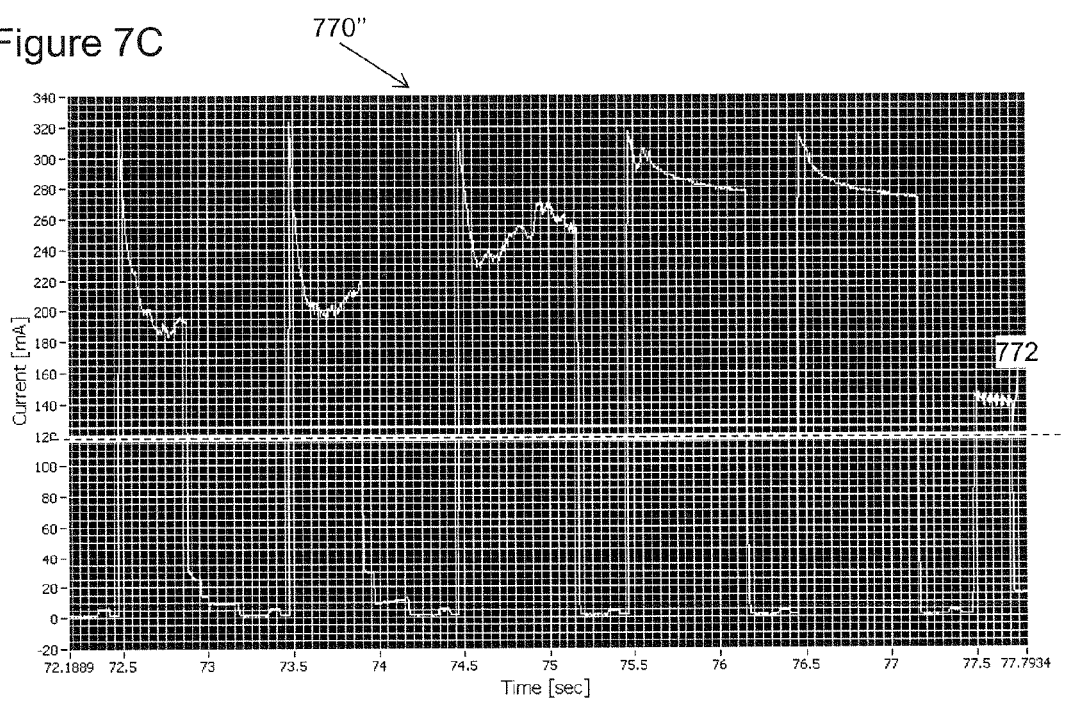

FIG. 7A, B, C illustrate close up views of experimental current vs. time data, in accordance with an exemplary embodiment of the invention. More specifically, in FIG. 7A graph 770 illustrates current vs. time behavior of the exemplary infuser during the disengagement period (from 12 to 17 sec on graph 670). In FIG. 7B, graph 770' illustrates current vs. time behavior of the exemplary infuser during normal operation while pumping medicine. In FIG. 7C, graph 770" illustrates current vs. time behavior of the exemplary infuser with an occlusion (from 72 to 77 sec on graph 670).

In FIG. 7A the transient current is strongly variable and dependent on sample timing. The peak current may rise to and/or above the 280 mA occlusion value.

Comparing graphs 770 and 770" it seen that the occlusion along with causing higher current also produces longer pulses of energy over time. A measure that includes for example both pulse width and current magnitude may be more sensitive to changes in injector status and/or more reliable than using just the current value as an indicator. For example the integral of current over time during a pulse may be used to account for changes both of the control parameter (pulse width) and the measured input (current magnitude).

For example, during disengaged (minimal load) conditions the pulse width is approximately 0.1 sec and the majority of the pulse is near the lower voltage baseline value of 125 mA. Therefore for each pulse the in the disengagement graph 770 the area under the curve is approximately 13 second×mA. For example, during normal pumping (engaged) conditions (as illustrated for example in graph 770') the pulse width is approximately 0.25 sec and the majority of the pulse is approximately of 180 mA. Therefore for each pulse the in the normal working graph 770' the area under the curve is approximately 45 second×mA. For example, during the occluded behavior (for example past 75 sec in graph 770"), exemplary pulse width is approximately 0.7 sec and the current is approximately 280 mA giving an area under the curve of approximately 200 second×mA.

For an infuser that includes short power cut offs to preserve controller voltage (for example as described herein above), power may be cut off to the motor when current is high. This may cause transient and/or an overall decrease the current when there is an occlusion. This may make changes in current a less reliable indicator of occlusions. The short term power cut offs may slow the motor. This may lead to a higher pulse width (for example when the controller extends the pulse to achieve the same rotation count). In that case, the integral of current over time indicator of occlusion would remain reliable (for example the reduced current due to short power cut offs may be offset by the increased pulse length and the integral under the pulse during occlusion would remain high).

Method of Ascertaining a Status of an Infuser

Figure 8:
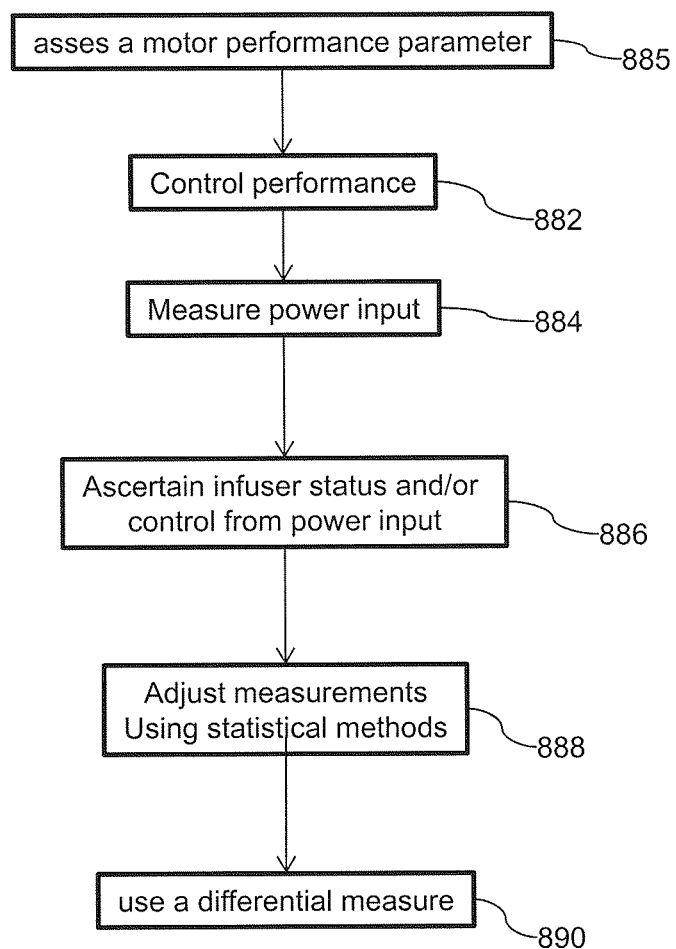
FIG. 8 is a flow chart illustrating a method of ascertaining a status of an infuser, in accordance with an exemplary embodiment of the invention.

FIG. 8 is a flow chart illustration of a method of ascertaining a status of an infuser.

In some embodiments performance an infuser may be assessed 885. Optionally assessing 885 may include coarse measurement of a performance parameter. For example a revolution counter may count revolutions of a motor. In some embodiments, a motor may revolve for example between 5 to 50 times during a power pulse period which may range from example 0.05 sec to 0.7 sec. For example the rotation frequency may range between 1/100 msec to 1/1 msec.

In some embodiments power input to an infuser may optionally be controlled 882. For example control may be via a negative feedback loop. For example a pumping rate of the infuser may be controlled by cutting off power to an actuator when the discharge in a period reaches a desired target. For example, input power may be reduced when a target discharge (which may be estimated, for example, from the number of motor rotations) is reached during designated in a time period. For example, when the infuser reaches the target discharge before the end of the time period, a power pulse may be shut off to a motor driving a pump. Alternatively or additionally, a negative feedback loop may regulate voltage input to a controller. When voltage falls to a controller, pulses of power may be diverted from a motor to the controller.

In some embodiments, the status of the infuser may be ascertained 886 by integrating motor power input with information on the motor control parameter. For example, the measured current magnitude (the measured parameter) may be integrated over the pulse time (the control parameter).

In some embodiments, power input to an actuator may be measured 884. For example the input current to the motor may be measured. For example measurements 884 may be made at a sample frequency. For example, a sample frequency may range between 1/1 msec and 1/100 msec.

In some embodiments, measured 884 power input and/or an ascertained parameter (for example the result of integration of current over time) may be adjusted 888 using statistical methods, for example a moving average and/or data smoothing.

In some embodiments, the sensitivity of the detection of statuses may be increased using 890 a differential measure. For example, due to variability of battery state and/or quality and/or variability in temperature and/or drug viscosity and/or internal resistance of components, absolute measures may not be robust. Nevertheless, a baseline measure may be calculated and changes may be interpreted to determine infuser status. For example, once a pumping status has been reached and a baseline determined, a large drop in the integral of current over pulse time may indicate a disengagement of the drive mechanism. For example, once a pumping status has been reached and a baseline determined, a large increase in the integral of current over pulse time may indicate an occlusion.

It is expected that during the life of a patent maturing from this application many relevant technologies will be developed and the scope of the terms used herein are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determining a status of a battery operated drug infusing device having an actuator, the method comprising:
   measuring an initial input energy level;
   determining whether the initial energy level is below a minimum threshold, above a maximum threshold, or represents a steady input energy state between the minimum and maximum thresholds;
   when the initial energy level is above the maximum threshold, triggering an alarm;
   when the initial energy level is below the minimum threshold, determining whether the initial energy level remains below the minimum threshold for a predetermined period of time, and if so, triggering an alarm;
   when the initial energy level is determined to be at the steady input energy state:
      establishing the steady input energy state as a baseline input energy; and
      controlling the actuator based on a performance of the actuator as determined by:
         (1) measuring an input parameter to the actuator, the input parameter including at least a magnitude of a current input to the actuator, and
         (2) ascertaining a status of the device by integrating a magnitude of said current input over a time corresponding to said current input to the actuator and comparing the integrated current input over time with the baseline input energy-inserted therein.

2. The method of claim 1, wherein
said performance of the actuator includes a cumulative movement of the actuator, and
said controlling includes limiting a time of current input to the actuator.

3. The method of claim 2, wherein said cumulative movement includes a number of revolutions by the actuator during a time period.

4. The method of claim 3, wherein said limiting includes limiting a pulse density of said current input in said time period.

5. The method of claim 1, wherein said controlling affects said input parameter.

6. The method of claim 5, wherein a result of said measuring serves as a proxy for a parameter of said controlling.

7. The method of claim 6, wherein a time dependence of said measured input parameter serves as said proxy for said parameter of said controlling.

8. The method of claim 1, wherein said controlling includes pulse density modulation and said ascertaining depends on said pulse density.

9. The method of claim 1, wherein said status includes at least one element selected from the group consisting of, a blockage, a disengagement, changing of an active mechanical part, discharging medicine, and not discharging.

10. The method of claim 1, wherein said controlling includes:
    counting a number of rotations by the actuator wherein said number of rotations is proportional to a cumulative discharge of the device, and
    cutting off said current when said number reaches a threshold.

11. The method of claim 10, wherein a rate of said counting is less than four times a sampling rate of said measuring.

12. The method of claim 1, wherein said input parameter is unregulated.

13. The method of claim 1, wherein said controlling includes temporarily cutting off said input parameter.

* * * * *

UNITED STATES PATENT AND TRADEMARK OFFICE
CERTIFICATE OF CORRECTION

PATENT NO. : 9,889,256 B2  
APPLICATION NO. : 13/886867  
DATED : February 13, 2018  
INVENTOR(S) : Oz Cabiri et al.

Page 1 of 1

It is certified that error appears in the above-identified patent and that said Letters Patent is hereby corrected as shown below:

In the Claims

In Claim 1, delete the phrase "baseline input energy-inserted therein" at Column 16, Lines 14-15, and insert the phrase --baseline input energy--.

Signed and Sealed this  
Twenty-fourth Day of July, 2018

Andrei Iancu  
*Director of the United States Patent and Trademark Office*